(12) United States Patent
Frick et al.

(10) Patent No.: US 7,615,536 B2
(45) Date of Patent: Nov. 10, 2009

(54) 1,4-BENZOTHIAZEPINE 1,1-DIOXIDE DERIVATIVE, PROCESS FOR ITS PREPARATION, MEDICAMENTS COMPRISING THIS COMPOUND, AND USE THEREOF AS A HYPOLIPIDAEMIC

(75) Inventors: Wendelin Frick, Frankfurt am Main (DE); Heiner Glombik, Frankfurt am Main (DE); Hubert Heuer, Frankfurt am Main (DE); Hans-Ludwig Schaefer, Frankfurt am Main (DE); Stefan Theis, Frankfurt am Main (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 108 days.

(21) Appl. No.: 11/970,281

(22) Filed: Jan. 7, 2008

(65) Prior Publication Data

US 2008/0207534 A1 Aug. 28, 2008

Related U.S. Application Data

(63) Continuation of application No. PCT/EP2006/006848, filed on Jul. 13, 2006.

(30) Foreign Application Priority Data

Jul. 15, 2005 (DE) .................. 10 2005 033 099

(51) Int. Cl.
*C07D 281/10* (2006.01)
*A61K 31/55* (2006.01)
*A61K 31/70* (2006.01)

(52) U.S. Cl. .................. 514/43; 514/23; 514/42; 536/22.1; 536/29.1; 536/29.13

(58) Field of Classification Search .......... None
See application file for complete search history.

(56) References Cited

U.S. PATENT DOCUMENTS 6,221,897 B1 * 4/2001 Frick et al. .......... 514/431
6,277,831 B1 * 8/2001 Frick et al. .......... 514/43

FOREIGN PATENT DOCUMENTS

| EP | 0153913 | 9/1985 |
| EP | 0864582 | 9/1998 |
| WO | WO 00/61568 | 10/2000 |

* cited by examiner

*Primary Examiner*—Traviss C McIntosh, III
(74) *Attorney, Agent, or Firm*—Barbara E. Kurys

(57) ABSTRACT

The invention relates to the compound of the formula (A) and also to its physiologically acceptable salts. The compound is suitable as, for example, a hypolipidemic

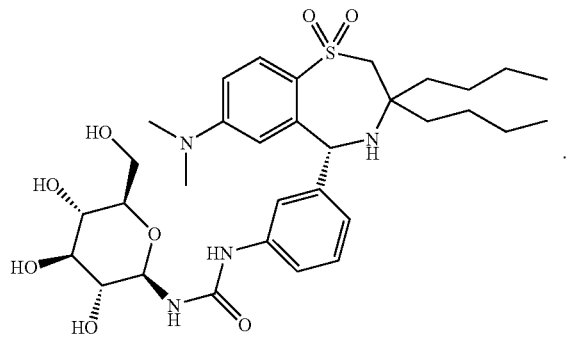

17 Claims, No Drawings

1,4-BENZOTHIAZEPINE 1,1-DIOXIDE DERIVATIVE, PROCESS FOR ITS PREPARATION, MEDICAMENTS COMPRISING THIS COMPOUND, AND USE THEREOF AS A HYPOLIPIDAEMIC

This application is a continuation of International application No. PCT/EP2006/006,848, filed Jul. 13, 2006, which is incorporated herein by reference in its entirety; which claims the benefit of priority of German Patent Application No. 10 2005 033 099.1, filed Jul. 15, 2005.

The invention relates to a substituted 1,4-benzothiazepine 1,1-dioxide derivative and to its physiologically acceptable salts.

1,4-Benzothiazepine 1,1-dioxide derivatives and their use for treating hyperlipidemia and also arteriosclerosis and hypercholesterolemia have already been described (EP 1 169 313).

It was an object of the invention to provide a compound which, compared to the compounds described in EP 1 169 313, has considerably better efficacy.

Accordingly, the invention relates to the compounds of the formula A

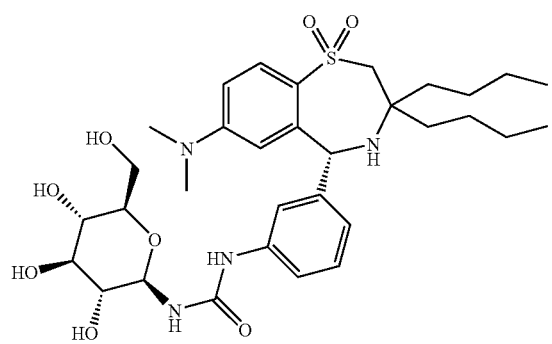

and their pharmaceutically acceptable salts.

Because they are more soluble in water than the starting compounds or the base compounds, pharmaceutically acceptable salts are particularly suitable for medical applications. These salts must possess a pharmaceutically acceptable anion or cation. Suitable pharmaceutically acceptable acid addition salts of the compound according to the invention are salts of inorganic acids, such as hydrochloric acid, hydrobromic acid, phosphoric acid, metaphosphoric acid, nitric acid and sulfuric acid, and also of organic acids, such as acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid.

Salts containing an anion which is not pharmaceutically acceptable, such as, for example, trifluoroacetate, also belong within the scope of the invention as useful intermediates for preparing or purifying pharmaceutically acceptable salts and/or for use in nontherapeutic applications, for example in-vitro applications.

The compound according to the invention can also be present in different polymorphic forms, for example as amorphous and crystalline polymorphic forms. All the polymorphic forms of the compound according to the invention belong within the scope of the invention and are another aspect of the invention.

In that which follows, all references to "compound(s) according to formula A" relate to the compound of the formula A as described above and to its salts and solvates.

The compound of the formula A can also be administered in combination with other active compounds.

The quantity of a compound according to formula A which is required in order to achieve the desired biological effect depends on a number of factors, e.g. the specific compound which is selected, the intended use, the type of administration and the clinical state of the patient. In general, the daily dose lies in a range from 0.01 mg to 100 mg (typically from 0.05 mg to 50 mg) per day per kilogram of body weight, e.g. 0.1-10 mg/kg/day.

Single dose formulations which can be administered orally, such as tablets or capsules, can, for example, contain from 1.0 to 1000 mg, typically from 10 to 600 mg. While the compounds according to formula A can themselves be used as the compound for treating the abovementioned conditions, they are preferably present, together with an acceptable carrier, in the form of a pharmaceutical composition. The carrier naturally has to be acceptable, in the sense that it is compatible with the other constituents of the composition and is not harmful to the health of the patient. The carrier can be a solid or a liquid or both and is preferably formulated with the compound as a single dose, for example as a tablet which can contain from 0.05% to 95% by weight of the active compound. Other pharmaceutically active substances can also be present, including other compounds according to formula A. The pharmaceutical compositions according to the invention can be prepared using one of the known pharmaceutical methods, which essentially consist in mixing the constituents with pharmacologically acceptable carrier substances and/or auxiliary substances.

Pharmaceutical compositions according to the invention are those which are suitable for oral and peroral (e.g. sublingual) administration even if the most suitable mode of administration depends, in each individual case, on the nature and severity of the condition to be treated and on the nature of the compound according to formula A which is in each case employed. Sugar-coated formulations and sugar-coated delayed-release formulations also belong within the scope of the invention. Formulations which are acid-resistant and gastric juice-resistant are preferred. Suitable gastric juice-resistant coatings include cellulose acetate phthalate, polyvinyl acetate phthalate, hydroxypropylmethyl cellulose phthalate and anionic polymers of methacrylic acid and methyl methacrylate.

Suitable pharmaceutical compounds for oral administration can be present in separate units, such as capsules, cachets, lozenges or tablets which in each case contain a specific quantity of the compound according to formula A; as powders or granulates; as a solution or suspension in an aqueous or non-aqueous liquid; or as an oil-in-water or a water-in-oil emulsion. As has already been mentioned, these compositions can be prepared using any suitable pharmaceutical method which includes a step in which the active compound and the carrier (which can consist of one or more additional constituents) are brought into contact. In general, the compositions are prepared by uniformly and homogeneously mixing the active compound with a liquid and/or finely divided solid carrier, after which the product is molded, if necessary. Thus, a tablet can be prepared, for example, by means of a powder or granulate of the compound being pressed or molded, where appropriate together with one or more additional constituents. Pressed tablets can be prepared by tableting the compound in freely flowing form, such as a powder or granulate, which is mixed, where appropriate, with a binder, lubricant, inert diluent and/or a (several) surface-active/dispersing agent(s) in a suitable machine. Molded tablets can be prepared by molding the pulverulent compound, which is moistened with an inert, liquid diluent, in a suitable machine.

Pharmaceutical compositions which are suitable for peroral (sublingual) administration include lozenges which contain a compound according to formula A together with a flavoring agent, usually sucrose and gum arabic or tragacanth, and pastils, which include the compound in an inert base such as gelatin and glycerol or sucrose and gum arabic.

A further embodiment of the pharmaceutical compositions according to the invention comprises suitable metal salts, such as, for example, calcium, aluminum, iron, copper, zinc, magnesium, manganese or zinc salts. Preference is given to calcium and zinc salts, such as, for example, calcium phosphate, calcium lactate, calcium carbonate, calcium gluconate, calcium acetate, zinc phosphate, zinc lactate, zinc carbonate, zinc gluconate or zinc acetate. The addition of these salts to the pharmaceutical composition may reduce or prevent the occurrence of diarrhea in the patient.

The following are suitable to use as additional active compounds for the combination preparations:

all the antidiabetics which are named in chapter 12 in the Roten Liste [Red List] 2005. They can be combined with compounds of the formula A according to the invention, particularly for the purpose of synergistically improving the effect. The active compound combination can be administered either by separately administering the active compounds to the patient or administering them in the form of combination preparations in which several active compounds are present in one pharmaceutical preparation. Most of the active compounds which are cited below are disclosed in USP Dictionary of USAN and International Drug Names, US Pharmacopeia, Rockville 2001.

Antidiabetics include insulin and insulin derivatives, such as Lantus or HMR 1964, rapidly acting insulins (see U.S. Pat. No. 6,221,633), GLP-1 derivatives, such as those which Novo Nordisk A/S has disclosed in WO 98/08871, Zealand has disclosed in WO 01/04156 and Beaufour-Ipsen has disclosed in WO 00/34331 and also orally active hypoglycemic active compounds.

The orally active hypoglycemic active compounds preferably include sulfonylureas, biguanidines, meglitinides, oxadiazolidinediones, thiazolidinediones, glucosidase and glycogen phosphorylase inhibitors, glucagon antagonists, GLP-1-agonists, potassium channel openers, such as those which Novo Nordisk A/S has disclosed in WO 97/26265 and WO 99/03861, insulin sensitizers, inhibitors of liver enzymes which are involved in stimulating gluconeogenesis and/or glycogenolysis, modulators of glucose uptake, glucose transport and glucose reabsorption, compounds which alter fat metabolism, such as antihyperlipidemic active compounds and antilipidemic active compounds, compounds which decrease food intake, PPAR agonists and PXR agonists, and active compounds which act on the ATP-dependent potassium channel in the beta cells.

In one embodiment of the invention, the compounds of the formula A are administered in combination with an HMG-CoA reductase inhibitor, such as simvastatin, fluvastatin, pravastatin, lovastatin, atorvastatin, cerivastatin or rosuvastatin.

In one embodiment of the invention, the compounds of the formula I are administered in combination with a cholesterol absorption inhibitor, such as ezetimibe, tiqueside, pamaqueside, or with a compound as described in PCT/EP 2004/00269, PCT/EP 2003/05815, PCT/EP 2003/05814, PCT/EP 2003/05816, EP 0114531 or U.S. Pat. No. 6,498,156.

In one embodiment of the invention, the compounds of the formula A are administered in combination with a PPAR gamma agonist, such as rosiglitazone, pioglitazone, JTT-501 or GI 262570.

In one embodiment of the invention, the compounds of the formula A are administered in combination with a PPAR alpha agonist, such as GW 9578 or GW 7647.

In one embodiment of the invention, the compounds of the formula A are administered in combination with a mixed PPAR alpha/gamma agonist, such as GW 1536, AVE 8042, AVE 8134 or AVE 0847, or as described in PCT/US 00/11833, PCT/US 00/11490 or WO 03/020269.

In one embodiment of the invention, the compounds of the formula A are administered in combination with a fibrate, such as fenofibrate, clofibrate or bezafibrate.

In one embodiment of the invention, the compounds of the formula A are administered in combination with an MTP inhibitor, such as implitapide, BMS-201038 or R-103757.

In one embodiment of the invention, the compounds of the formula A are administered in combination with a CETP inhibitor, such as JTT-705.

In one embodiment of the invention, the compounds of the formula A are administered in combination with a polymeric bile acid adsorber, such as cholestyramine or colesevelam.

In one embodiment of the invention, the compounds of the formula A are administered in combination with an LDL receptor inducer (see U.S. Pat. No. 6,342,512).

In one embodiment of the invention, the compounds of the formula A are administered in combination with an ACAT inhibitor, such as avasimibe.

In one embodiment of the invention, the compounds of the formula A are administered in combination with an antioxidant, such as OPC-14117.

In one embodiment of the invention, the compounds of the formula A are administered in combination with a lipoprotein lipase inhibitor, such as NO-1886.

In one embodiment of the invention, the compounds of the formula A are administered in combination with an ATP citrate lyase inhibitor, such as SB-204990.

In one embodiment of the invention, the compounds of the formula A are administered in combination with a squalene synthetase inhibitor, such as BMS-188494.

In one embodiment of the invention, the compounds of the formula A are administered in combination with a lipoprotein (a) antagonist, such as CI-1027 or nicotinic acid.

In one embodiment of the invention, the compounds of the formula A are administered in combination with a lipase inhibitor, such as orlistat.

In one embodiment of the invention, the compounds of the formula A are administered in combination with insulin.

In one embodiment, the compounds of the formula A are administered in combination with a sulfonylurea, such as tolbutamide, glibenclamide, glipizide or glimepiride.

In one embodiment, the compounds of the formula A are administered in combination with a biguanide, such as metformin.

In yet another embodiment, the compounds of the formula A are administered in combination with a meglitinide, such as repaglinide.

In one embodiment, the compounds of the formula A are administered in combination with a thiazolidinedione, such as troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione. In one embodiment, the compounds of the formula A are administered in combination with an α-glucosidase inhibitor, such as miglitol or acarbose.

In one embodiment, the compounds of the formula A are administered in combination with an adenosine A1 agonist such as those which are described in EP 0912520 or PCT/EP06749.

In one embodiment, the compounds of the formula A are administered in combination with an active compound which acts on the ATP-dependent potassium channel of beta cells, such as tolbutamide, glibenclamide, glipizide, glimepiride or repaglinide.

In one embodiment, the compounds of the formula A are administered in combination with more than one of the abovementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment, the compounds of the formula A are administered in combination with CART modulators (see "cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid-{4-[(4-aminoquinazolin-2-ylamino)methyl]cyclohexyl-methyl}amide hydrochloride (CGP 71683A)), cannabinoid receptor 1 antagonists (see, e.g., EP 0656354, WO 00/15609 or WO 02/076949) MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl] amide; (WO 01/91752)), orexin antagonists (e.g. 1-(2-methylbenzoxazol-6-yl)-3-[1,5]naphthyridin-4-yl urea hydrochloride (SB-334867-A)), H3 agonists (3-cyclohexyl-1-(4,4-dimethyl-1,4,6,7-tetrahydroimidazo[4,5-c]pyridin-5-yl)-propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3-agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, MCH (melanin-concentrating hormone) receptor antagonists (see, e.g., WO 03/15769), CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), or SR-146131 (WO 0244150) or SSR-125180), serotonin reuptake inhibitors (e.g. dexfenfluramine), mixed serotoninergic and noradrenergic compounds (e.g. WO 00/71549), 5HT agonists, e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (tert-butyl 6-benzyloxy-1-(2-diisopropylaminoethylcarbamoyl)-3,4-dihydro-1H-isoquinoline-2-carboxylate (WO 01/85695)), TRH agonists (see, e.g. EP 0 462 884) uncoupling protein 2 or protein 3 modulators, leptin agonists (see, e.g. Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, doprexin), lipase/amylase inhibitors (e.g. WO 00/40569), PPAR modulators (e.g. WO 00/78312), 11β-HSD1 (11-beta-hydroxysteroiddehydrogenase type 1) inhibitors (see e.g. WO 01/90094 or T. Barf et al., J. Med. Chem. (2002), 45, 3813-3815), acetyl-CoA carboxylase (ACC; see e.g. WO 99/46262) inhibitors, dipeptidylpeptidase IV (DPP-IV; see e.g. EP 1259246) inhibitors, RXR modulators or TR-β-agonists.

In one embodiment of the invention, the other active compound is leptin; see, e.g., "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active compound is dexamphetamine or amphetamine.

In one embodiment, the other active compound is fenfluramine or dexfenfluramine.

In yet another embodiment, the other active compound is sibutramine.

In one embodiment, the other active compound is orlistat.

In one embodiment, the other active compound is mazindol or phentermine.

In one embodiment, the compounds of the formula A are administered in combination with ballast substances, preferably insoluble ballast substances (see, e.g., carob/Caromax®) (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hoechst, 65926 Frankfurt/Main)). The combination with Caromax® can be effected in one preparation or by means of separating administering compounds of the formula A and Caromax®. In this connection, Caromax® can also be administered in the form of foodstuffs, for example in bread, cakes and pastries or muesli bars.

It will be understood that each suitable combination of the compounds according to the invention with one or more of the abovementioned compounds and, if desired, one or more additional pharmacologically active substances, is regarded as coming within the protected scope of the present invention.

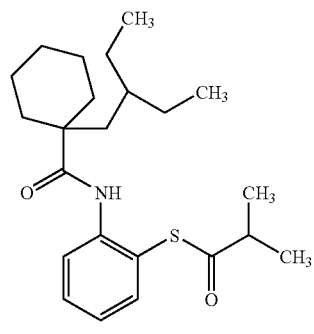

JTT-705

-continued
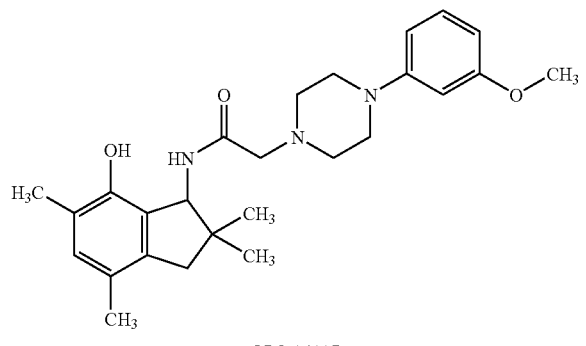
OPC-14117
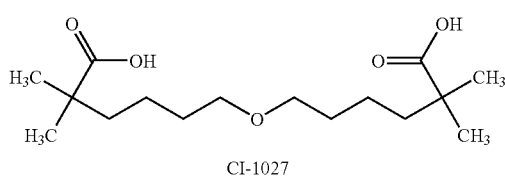
SB-204990
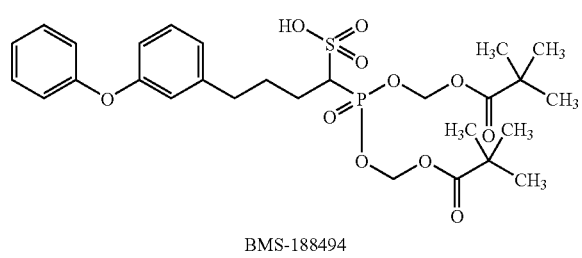
NO-1886
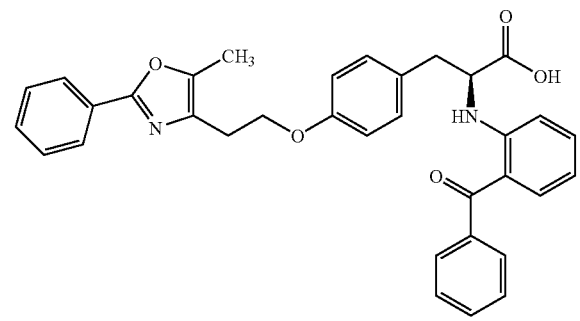
CI-1027
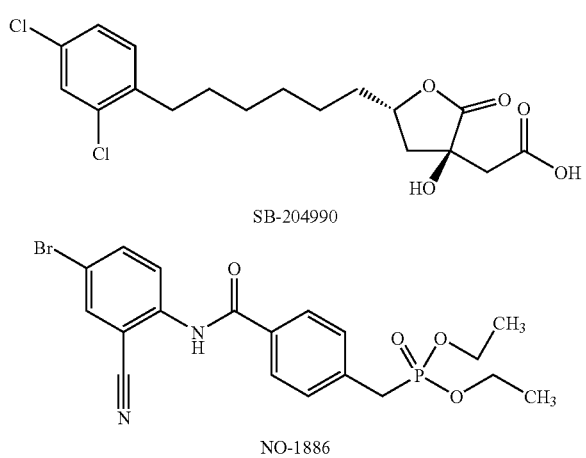
BMS-188494
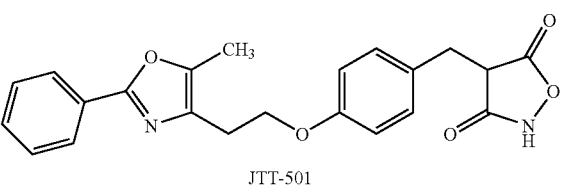
JTT-501
EXAMPLE A
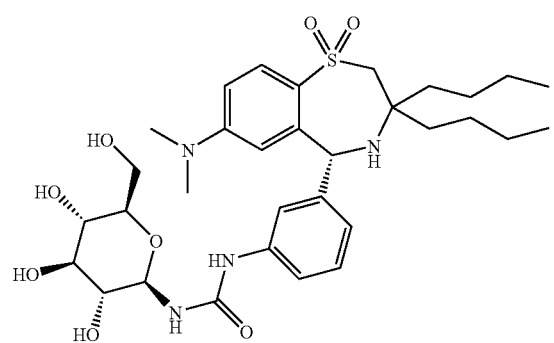
Compound A was prepared as follows:
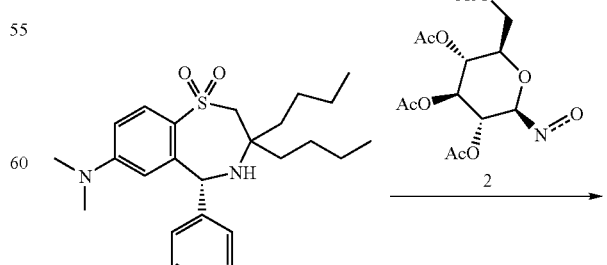
GI 262570

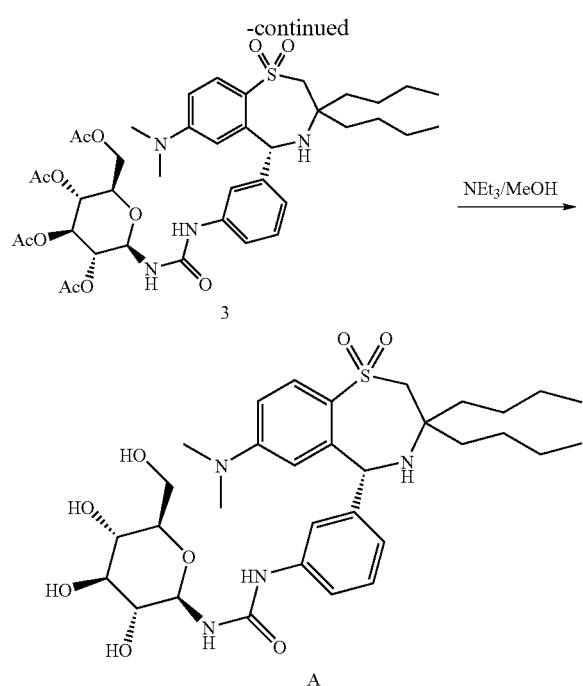

Synthesis of Compound 1a:

The enantiomerically pure compound 1a is obtained from the racemic anilide 1 (EP 1 169 313 compound 8a/b) by chiral chromatography using Chiralpak AS-H76 with the mobile phase n-heptane/methanol/ethanol 10/1/1 plus 0.1% DEA. By crystallization from THF/EA/n-heptane, it is possible to purify compound 1a even further (ee 99.9%). The eutomer has a positive optical rotation, and the absolute stereochemistry was determined by single crystal X-ray structure.

Synthesis of Compound 3:

At room temperature, 6 g of anilide 1a and 7.5 g of isocyanate 2 (Synlett 2003, 1, 47-50) are dissolved in 150 ml of methylene chloride. After one hour at room temperature, the mixture is concentrated and the residue is purified by flash chromatography. Yield 10.5 g (95%) of 3 as a colorless solid. TLC (n-heptane/ethyl acetate 1:2). $R_f$=0.3. $C_{40}H_{56}N_4O_{12}S$ (816.98). MS (M+H)$^+$=817.33.

Synthesis of Compound A:

9.7 g of 3 are dissolved in 120 ml of methanol and 40 ml of triethylamine and allowed to stand at room temperature for 16 hours. The solution is concentrated and the residue is dissolved in 60 ml of hot ethyl acetate. After cooling to room temperature, 50 ml of ethyl acetate/n-heptane (4:1) are added. The suspension is stirred for 30 minutes, the precipitate is filtered off with suction and washed with 30 ml of ethyl acetate/n-heptane (4:1). Yield 7.01 g (91%) of A as an amorphous solid and 450 mg of mother liquor (contains 40-50% of A). TLC (methylene chloride/methanol/conc. ammonia 30/10/3). $R_f$=0.5. $C_{32}H_{48}N_4O_8S$ (648.83). MS (M+H)$^+$= 649.26.

Biological testing of the compound A according to the invention was carried out using the in vitro IBAT inhibition test. This test examines the effect of the compound according to the invention on the transport activity of the recombinantly expressed human sodium-dependent ileal bile acid transporter (IBAT=ileal Na$^+$/bile acid contransporter,
ASBT=apical sodium-dependent bile acid transporter, SLC10A2=solute carrier family 10, member 2).

Preparation for and practice of the in vitro IBAT inhibition test:

1. Cloning of an Expression Vector for Human IBAT

The cDNA (complementary deoxyribonucleic acid) of human IBAT was cloned using standard methods of molecular biology as described, for example, in Molecular Cloning: A Laboratory Manual, by Joseph Sambrook and David Russell, and introduced into the pcDNA1 vector from Invitrogen. Subsequent sequencing of the insert showed complete identity with bases 599 to 1645 of the base sequence for the human IBAT described by P. A. Dawson and deposited at the GenBank sequence databank (GenBank Accession Number: U10417). Bases 599 to 1645 correspond to the complete coding region of the human IBAT.

2. Preparation of a Recombinant Cell Line with Constitutive Expression of Human IBAT The expression vector for the human IBAT was introduced by means of stable transfection into CHO (Chinese hamster ovary) cells. To select single cell clones, 400 μg/ml of geneticin was added to the cell culture medium (Ham's F12 medium supplemented with 10% fetal calf serum, 100 units/ml of penicillin, 100 units/ml of streptomycin). The functionality of the single cell clones resulting from the selection was tested via their uptake activity for radioactively labeled taurocholic acid ([$^3$H]-TCA). The cell clone having the highest uptake activity for [$^3$H]-TCA, subsequently shown as CHO-hIBAT, was selected for further tests and cultivated further in the presence of 400 μg/ml of geneticin.

3. Measurement of the Inhibitory Effect of the Compound According to the invention on IBAT-dependent uptake of taurocholic acid into cells CHO-hIBAT cells were sown at a concentration of 40 000 cells per well in cell culture medium in poly-D-lysine-coated 96-well plates and cultivated for 24h. The cells were then washed once with sodium-free transport assay buffer (140 mM choline chloride, 2 mM potassium chloride, 1 mM magnesium chloride, 1 mM calcium chloride, 10 mM HEPES/Tris, ph 7.5) and then incubated either with sodium-free transport assay buffer as negative control or with sodium-comprising transport assay buffer (140 mM sodium chloride, 2 mM potassium chloride, 1 mM magnesium chloride, 1 mM calcium chloride, 10 mM HEPES/Tris, ph 7.5) as positive control, at room temperature for 30 min. At the same time, the test wells were also incubated in the presence of different concentrations of the compound to be examined in sodium-comprising transport assay buffer, at room temperature for 30 min. Using a 10 mM stock solution in dimethyl sulfoxide, the test substances were appropriately diluted in transport assay buffer (40 μl/well). The test was then started by addition of 10 μl/well of a mixture of radioactively labeled taurocholic acid ([$^3$H]-TCA) and unlabeled taurocholic acid. The final concentration of taurocholic acid in the test was 10 μM. After an incubation time of 60 min at room temperature, the reaction was stopped by addition of 100 μl/well of sodium-free transport assay buffer (4° C.), and each well was washed three times with sodium-free transport assay buffer. Finally, 100 μL of scintillation fluid were added to each well, and the radioactivity taken up into the cells was determined in a MicroBeta scintillation microplate reader from Wallac.

The half-maximal inhibitory effect of the test compound (IC50 value, inhibitory concentration 50) was determined as follows:
1. Determination of the value for 0% inhibition. This is the value measured in the absence of substance, measured in sodium-comprising transport assay buffer.
2. Determination of the value for 100% inhibition. This is the value measured in the absence of substance, measured in sodium-free transport assay buffer.
3. Calculation of the inhibitory values, in percent, of the measurements which have been carried out in the presence of various concentrations of the compound to be examined. Using these values, it was then possible to determine the compound concentration at which taurocholic acid uptake was reduced by 50% (IC50 value).

For Example A, IC50 (human IBAT) was found to be: 0.057 μM

For comparison, the structurally most similar compound from EP 1 169 313 was also measured. For compound 11a (from Example 5) of the formula:

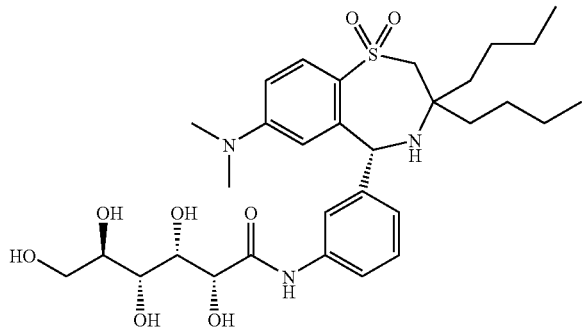

11a the IC50 (human IBAT) was found to be: 0.319 μM

Compared to this comparative example from EP 1 169 313, the activity of compound A according to the invention is 560% higher.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula A

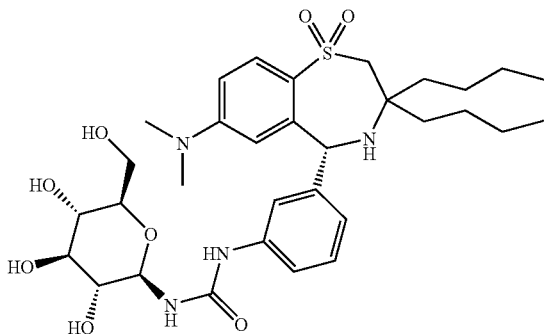

A or a pharmaceutically acceptable salt thereof.

2. A pharmaceutical composition comprising compound of formula A according to claim 1 in combination with at least one pharmaceutically acceptable excipient.

3. The composition according to claim 2 further comprising at least one other active compound.

4. The composition according to claim 3, wherein said other active compound normalizes lipid metabolism.

5. The composition according to claim 3, wherein said other active compound is selected from one or more antidiabetics, hypo-glycemically active compounds, anti-adipose drugs, anorectics, HMG-CoA-reductase inhibitors, cholesterol absorption inhibitors, PPAR gamma agonists, PPAR alpha agonists, PPAR alpha/gamma agonists, fibrates, MTP inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein (a) antagonists, lipase inhibitors, insulins, sulfonylureas, biguanides, meglitinides, thiazolidinediones, α-glucosidase inhibitors, active compounds acting on the ATP-dependent potassium channel of beta cells, CART agonists, NPY agonists, cannabinoid receptor 1 antagonists, MCH receptor antagonists, MC4 agonists, orexin agonists, H3 agonists, TNF agonists, CRF agonists, CRF BP antagonists, GLP-1 derivatives, urocortin agonists, β3 agonists, MSH (melanocyte-stimulating hormone) agonists, CCK-A agonists, serotonin reuptake inhibitors, mixed serotonin and noradrenergic compounds, 5HT agonists, bombesin agonists, galanin antagonists, growth hormones, growth-hormone-releasing compounds, TRH agonists, decoupling protein-2 or -3 modulators, leptin agonists, DA agonists (bromocriptine, doprexin), lipase/amylase inhibitors, 11β-HSD1 inhibitors, ACC inhibitors, DPP-IV inhibitors, PPAR modulators, RXR modulators or TR-β-agonists or amphetamines.

6. The composition according to claim 4, wherein said other active compound is selected from one or more antidiabetics, hypo-glycemically active compounds, anti-adipose drugs, anorectics, HMG-CoA-reductase inhibitors, cholesterol absorption inhibitors, PPAR gamma agonists, PPAR alpha agonists, PPAR alpha/gamma agonists, fibrates, MTP inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein (a) antagonists, lipase inhibitors, insulins, sulfonylureas, biguanides, meglitinides, thiazolidinediones, α-glucosidase inhibitors, active compounds acting on the ATP-dependent potassium channel of beta cells, CART agonists, NPY agonists, cannabinoid receptor 1 antagonists, MCH receptor antagonists, MC4 agonists, orexin agonists, H3 agonists, TNF agonists, CRF agonists, CRF BP antagonists, GLP-1 derivatives, urocortin agonists, β3 agonists, MSH (melanocyte-stimulating hormone) agonists, CCK-A agonists, serotonin reuptake inhibitors, mixed serotonin and noradrenergic compounds, 5HT agonists, bombesin agonists, galanin antagonists, growth hormones, growth-hormone-releasing compounds, TRH agonists, decoupling protein-2 or -3 modulators, leptin agonists, DA agonists (bromocriptine, doprexin), lipase/amylase inhibitors, 11β-HSD1 inhibitors, ACC inhibitors, DPP-IV inhibitors, PPAR modulators, RXR modulators or TR-β-agonists or amphetamines.

7. The composition according to claim 2, which comprises, as further auxiliary, one or more metal salts.

8. The composition according to claim 3, which comprises, as further auxiliary, one or more metal salts.

9. The composition according to claim 4, which comprises, as further auxiliary, one or more metal salts.

10. The composition according to claim 5, which comprises, as further auxiliary, one or more metal salts.

11. The composition according to claim 6, which comprises, as further auxiliary, one or more metal salts.

12. A method for the treatment of disorders of lipid metabolism in a patient comprising administering to said patient a therapeutically effective amount of a compound according to claim 1 or a pharmaceutically acceptable salt thereof.

13. A process for preparing a medicament comprising the compound of formula A according to claim 1, which comprises mixing the compound of formula A or a pharmaceutically acceptable salt thereof with a pharmaceutically acceptable carrier and bringing this mixture into a form suitable for administration.

14. A method for the treatment of hyperlipidemia in a patient comprising administering to said patient a therapeutically effective amount of a compound according to claim 1 or a pharmaceutically acceptable salt thereof.

15. A method for lowering the serum cholesterol concentration in a patient comprising administering to said patient a therapeutically effective amount of a compound according to claim 1 or a pharmaceutically acceptable salt thereof.

16. A method for treating arteriosclerotic symptoms in a patient comprising administering to said patient a therapeutically effective amount of a compound according to claim 1 or a pharmaceutically acceptable salt thereof.

17. A method for treating insulin resistance in a patient comprising administering to said patient a therapeutically effective amount of a compound according to claim 1 or a pharmaceutically acceptable salt thereof.

* * * * *